United States Patent [19]
Patel

[11] Patent Number: 5,632,731
[45] Date of Patent: May 27, 1997

[54] NON-ADHERENT WOUND DRESSING

[75] Inventor: Harish A. Patel, Norfolk, Mass.

[73] Assignee: The Kendall Company, Mansfield, Mass.

[21] Appl. No.: 345,060

[22] Filed: Nov. 25, 1994

[51] Int. Cl.$^6$ .................................................. A61F 13/00
[52] U.S. Cl. ................... 602/59; 602/47; 602/54; 604/307; 604/378
[58] Field of Search ................... 604/378–379, 604/304, 307; 602/41–43, 47, 54, 58

[56] References Cited

U.S. PATENT DOCUMENTS

| | | | |
|---|---|---|---|
| 3,703,897 | 11/1972 | Mack | 602/47 |
| 4,588,400 | 5/1986 | Ring et al. | 604/304 |
| 4,804,379 | 2/1989 | Toth | 604/378 |
| 4,994,037 | 2/1991 | Bernardin | 604/378 |
| 5,052,381 | 10/1991 | Gilbert | 602/47 |
| 5,167,613 | 12/1992 | Karami | 602/42 |
| 5,244,457 | 9/1993 | Karami | 602/55 |
| 5,252,374 | 10/1993 | Larsonneur | 608/378 |
| 5,294,478 | 3/1994 | Wanek | 604/378 |
| 5,304,161 | 4/1994 | Noel | 604/378 |
| 5,306,267 | 4/1994 | Hahn | 604/378 |
| 5,374,260 | 12/1994 | Lemay | 604/378 |
| 5,382,245 | 1/1995 | Thompson | 604/378 |
| 5,387,208 | 2/1995 | Ashton | 604/378 |

OTHER PUBLICATIONS

Websters II: The New Riverside University Dictionary, pp. 873 and 875.

*Primary Examiner*—Michael Powell Buiz
*Assistant Examiner*—Chalin Smith
*Attorney, Agent, or Firm*—David J. Koris, Esq.

[57] ABSTRACT

Disclosed is an improvement in wound dressings comprising an absorbent pad for receiving and retaining wound fluids sandwiched between outer perforated non-adherent films for preventing the dressing from sticking to the wound, the improvement being employing as the absorbent pad a multilayer structure comprising an inner layer of a low density absorbent material for receiving fluids diffusing to the dressing from the wound and an overlying layer of a high density absorbent material for receiving and retaining wound fluids diffusing through the inner layer in order to inhibit skin maceration due to the wetness of the surface area of the absorbent pad adjacent the wound.

6 Claims, 2 Drawing Sheets

NON-ADHERENT WOUND DRESSING

BACKGROUND OF THE INVENTION

As is well recognized in the art, ideally a wound dressing comprising an absorbent material providing a reservoir for the wound fluids diffusing from the wound should not interfere with normal wound healing. Yet, where the dressing comprises an absorbent pad of a fibrous material such as gauze which is in immediate contact with the wound, the diffusing wound fluid will extend into the interstices and around the fibers of the dressing so that the dressing is eventually adhesively and mechanically anchored into the wound surface, e.g. to graft sites, buds of new tissue forming over the wound or to the scabby protective covering for the wound.

Consequently, removal or changing of the dressing can and will cause disruption of the healing process delaying the healing process as well as being a painful procedure for the patient.

For these reasons, wound dressings have been well known and have received wide commercial acceptance wherein the absorbent material is sandwiched between outer perforated non-adherent films preventing the dressing from sticking to the wound.

As an example of such commercial dressings, mention may be made of the TELFA® adhesive dressings and pads and the TELFA® adhesive island dressings commercially available from the Kendall Healthcare Products Company, a division of The Kendall Company, assignee of the present invention.

While they are highly efficacious in that they provide the desired protective absorbent dressing while preventing adherence to the wound, they nevertheless tend to cause skin maceration if the dressing is not changed once it becomes saturated with wound fluid. Additionally, the pooling of wound fluid on the wound surface once the dressing becomes saturated tends to diffuse laterally to undermine the adhesive outside the wound area holding the dressing to the skin.

Stated simply, the task of the present invention is to inhibit maceration in such dressings and/or to reduce the number of times the dressing need to be changed, to prevent maceration.

BRIEF DESCRIPTION OF THE INVENTION

In accordance with this invention the task is solved by replacing the single absorbent layer pad with a multiple layer one comprising at least an inner low density absorbent layer for receiving fluid diffusing from the wound and an overlying high density layer for receiving and retaining fluid diffusing through the underlying low density absorbent layer. Optionally, a third absorbent layer which is low density like the inner absorbent layer is disposed over the high density absorbent layer.

In the preferred embodiment of the invention the dressing is a so-called island dressing wherein the absorbent pad is substantially centrally disposed on an adhesive layer of greater dimensions so that free adhesive surface surrounds the periphery of the absorbent pad for securing the dressing to the skin.

DETAILED DESCRIPTION OF THE INVENTION

As heretofore mentioned, the present invention is directed to an improvement in dressings wherein an absorbent material providing a reservoir for wound fluids diffusing thereto is disposed between opposed non-adhering perforated films or sheet materials.

The nature and objects of the invention will be best understood by reference to the drawings illustrating the preferred form of the invention taken in conjunction with the following detailed description.

Figure 1:
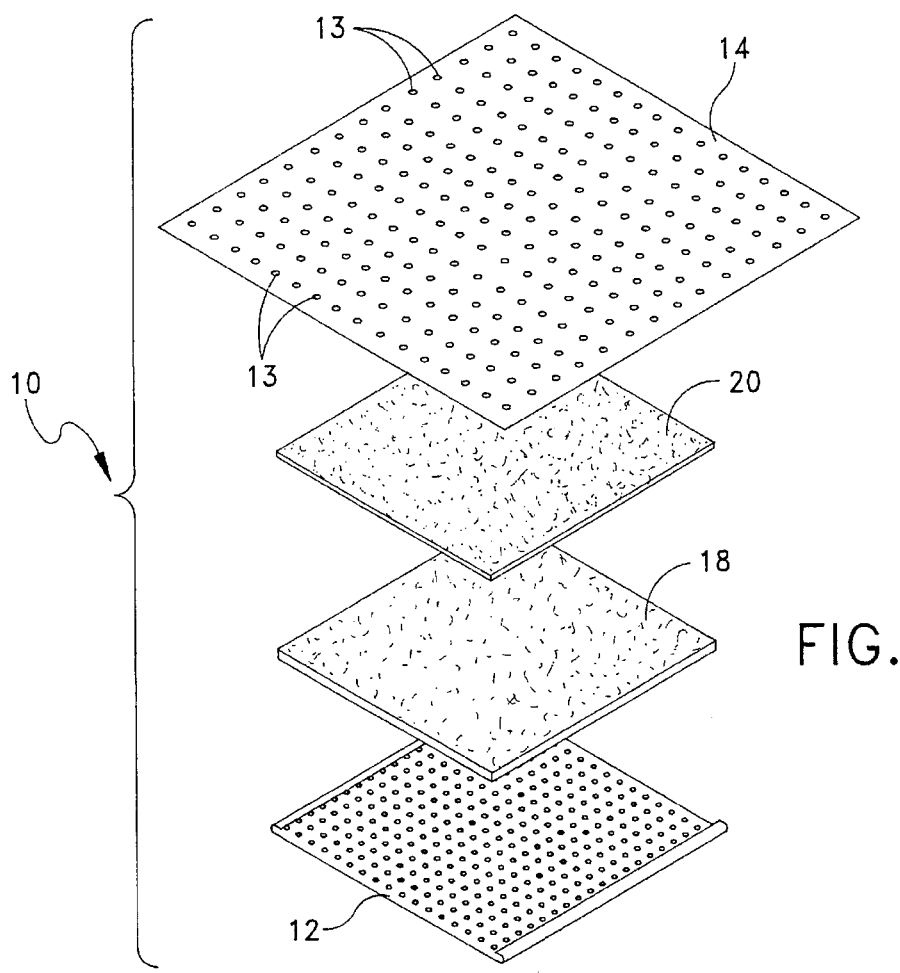
FIG. 1 is an exploded view showing the essential elements of one embodiment of the invention.
Figure 2:
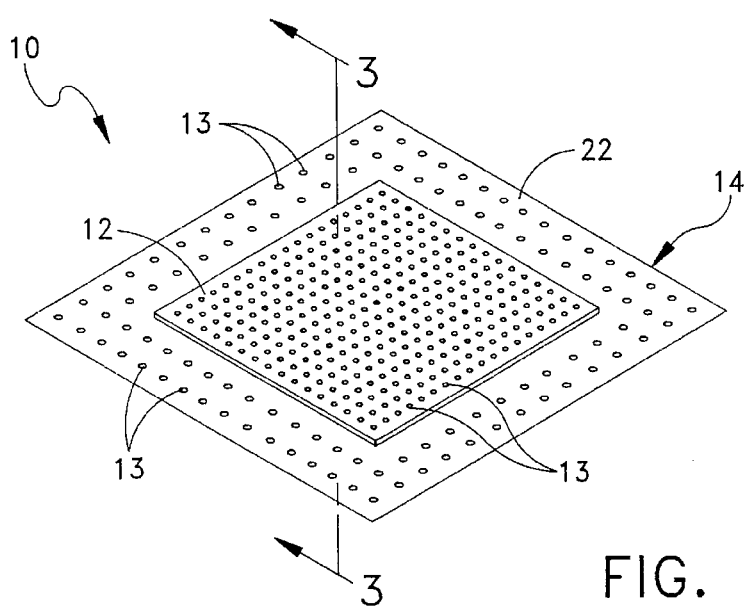
FIG. 2 is a perspective view of the side of the dressing to be applied to cover a wound.
Figure 3:
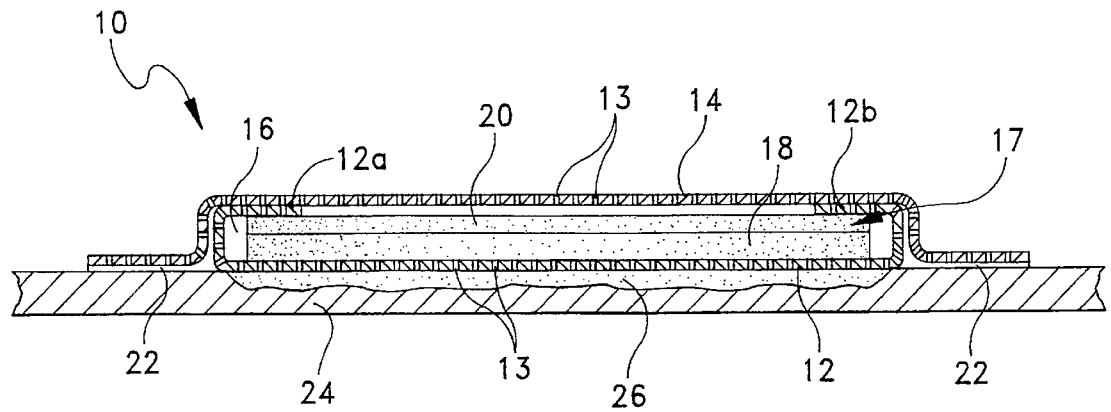
FIG. 3 is a sectional view taken along line 3—3 of FIG. 2.

FIGS. 1–3 relate to an island dressing in accordance with this invention. As shown therein, dressing (10) has perforated sheets (12) (14) defining a chamber (16) in which is disposed an absorbent pad (17) for receiving and retaining wound fluids diffusing within the chamber (16) through porous film (12), the absorbent pad (17) consisting of contiguous absorbent layers (18) and (20), layer (18) being a low density absorbent material and layer (20) being a high density absorbent material, as will be described in detail hereinafter. As seen in FIG. 3, perforated sheet (12) is wrapped around the edges of absorbent pad (17) with its edges (12a) (12b) overlapping the upper surface of the absorbent pad.

As seen in FIG. 2, sheet (14) has a layer of pressure-sensitive adhesive (22) on its inner surface, that is, the surface facing perforated sheet (12). The absorbent pad (17), which is of substantially smaller dimensions than sheet (14), is substantially centrally seated on the adhesive surface (22) of sheet (14), thereby securing pad (17) and the edges (12a) (12b) of sheet (12) to sheet (14), thus providing an island dressing adapted for securing the dressing (10) to the skin (24) of a patient surrounding a wound (26).

The difference between the dressing shown in FIGS. 1–3 and described above and island dressing such as the TELFA® adhesive island dressings sold for many years by the present assignee, which difference is the essence of the improvement upon which patentable novelty is here predicated, is the concept of providing, for the absorbent pad what may be said to be a two-layer pad structure with the inner layer to be positioned closest to the wound surface being of a low density material, the upper layer superposed thereover being of a high density material.

The concept of providing a wound dressing having a low density/high density absorbent pad structure is per se old, being disclosed, for example, in U.S. Pat. Nos. 5,167,613 and 5,244,457 issued to Karami et al and assigned to the assignee of the present invention.

As described therein, while the reservoir for receiving wound fluids in the described dressings may comprise any of the fabric materials heretofore employed to retain exudate, e.g. cotton, gauze sponges, absorbent pads such as those customarily used for abdominal surgery, and the like, they will most preferably consist of two separate but contiguous elements, namely a lower high density woven or non-woven fabric having optimum spreading or wicking characteristics and an upper low density fabric having optimum absorption capacity. Preferably, the high density fabric will have a density of on the order of 0.1 to 0.2 gms/(cm)$^3$; while the low density fabric will have a density less than 0.1 gm/(cm)$^3$, e.g. on the order of 0.05 gm/(cm)$^3$. The combination of the two fabrics will typically provide a weight per surface area of on the order of 7 ounces/square yard, the ratio of low:high density by thickness being on the order of about 3:1 to about 5:1. The fabrics may be woven or non-woven materials, non-woven being preferred, and illustrative fibers include rayon, rayon/polyester or polyester/cotton blends, cotton, cellulosic materials, etc.

In the wound dressing which is the subject matter to which the aforementioned patents are directed, the purpose of having high density fabric nearest the wound is to provide optimum spreading or wicking characteristics in order to facilitate exudate being absorbed over substantially the entire surface area of the absorbent fabric; while the upper or overlying low density woven or non-woven fabric possesses optimum absorption capacity, the composite absorbing fabric thereby providing maximum efficiency of the fabric for absorbing wound exudate before become saturated so as to require a dressing change.

While the present invention employs the same materials as described above, it will be seen that the task is different and accordingly the order of the two fabrics is reversed so that the low density fabric for optimum absorption is nearest the wound, thereby distinguishing over the teaching of the aforementioned patents.

Figure 4:
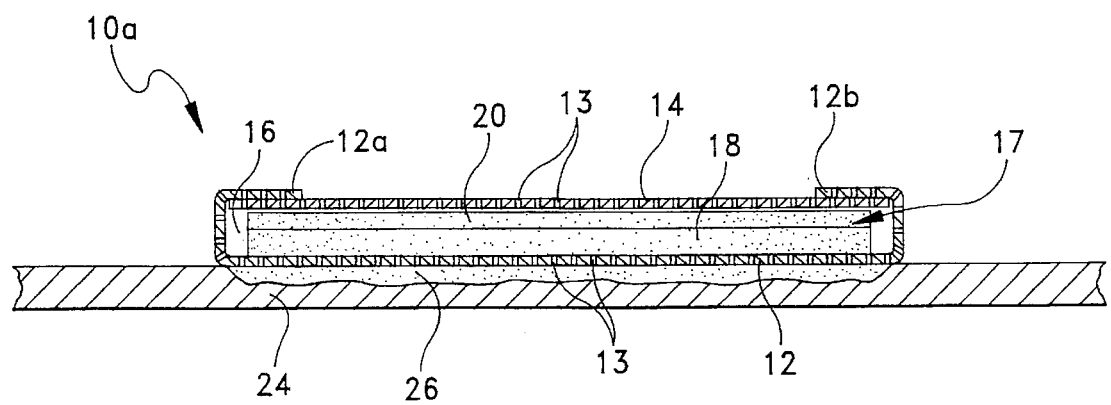
FIG. 4 is a view similar to FIG. 3 showing another embodiment of this invention.

FIG. 4 relates to an alternate embodiment of the invention wherein, unlike the island dressing of FIGS. 1–3, the dressing (10a) does not itself contain a free adhesive surface to adhere the dressing to the skin. Instead, as shown, perforate sheet (12) is somewhat larger than perforate sheet (14), with it free edges extending over sheet (14) and being secured thereto, e.g. by heat sealing or by adhesive means such as a pressure-sensitive adhesive, in order to enclose the reservoir (16) containing the absorptive pad (17).

As will be appreciated, the wound dressing (10a) may be secured to the skin by means of adhesive tape strips.

Figure 5:
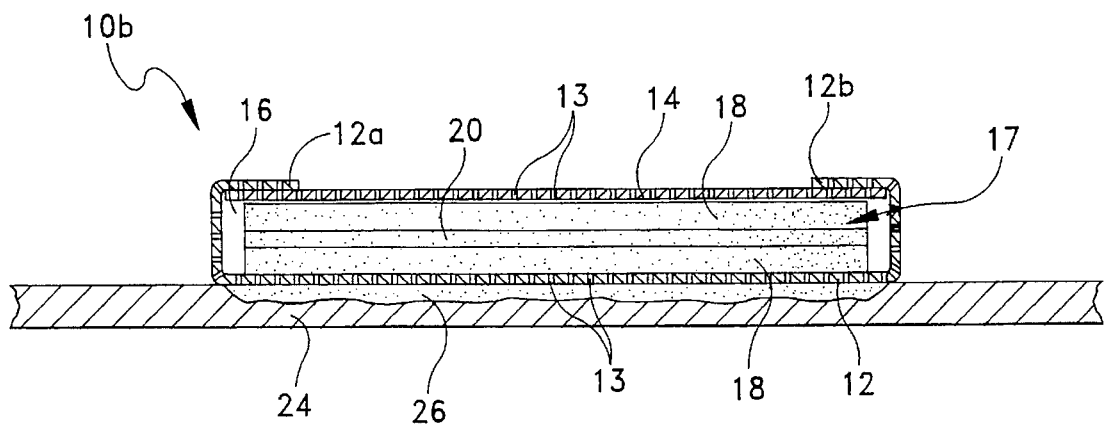
FIG. 5 is also a view similar to FIG. 3 of still another embodiment of this invention.

FIG. 5 relates to another embodiment in which the dressing (10b) is similar to the dressing (10a) of FIG. 4 in the sense that the dressing is not an island dressing, the distinction being that dressing (10b) is symmetrical in that it contains an outer layer of low density fabric (18) so that the absorptive pad (17) consists of a layer of high density fabric (20 sandwiched between outer layers (18) of low density fabric.

The embodiment of FIG. 5 offers the advantage of there being no difference which side of the dressing is applied over the wound; while the embodiment of FIG. 4 will require some indicia (not shown) indicating what side should be taped to the skin.

The perforated films to be employed for sheets (12) (14) are pr se old and known in the art. Accordingly, their selection comprises no part of this invention and will be a matter of choice within the expected judgment of the skilled worker.

By way of illustration, the selected film should be relatively thin, e.g. on the order of 10 mil or less, should possess a high degree of conformability and, of course, be non-toxic or in any way delay wound healing. The perforations (13) in the films should be sufficient to permit wound exudate to diffuse through the film at a rate which precludes pooling on the wound to cause maceration. For example, there may be on the order of 370–390 perforations per square inch having a diameter on the order of 0.020–0.040 inch. Suitable materials for sheets (12) (14) include polyesters, polyolefins and the like polymeric materials.

The adhesive to be employed for layer (22) may be any of the so-called medical grade or hypoallergenic pressure-sensitive adhesives heretofore employed for wound dressings and medical tapes. Such known adhesives include the rubber-based, acrylic, vinyl ether and hydrocolloid pressure-sensitive adhesives. The adhesive (22) may be coated to provide a layer at least 1 mil thick, preferably at least 5 mils thick.

While not an essential part of the invention, it will be appreciated that the island dressing (10) should also have a standard release sheet covering the free adhesive layer (22) in order to prevent premature and unwanted adherence of the adhesive to a substrate.

Since certain changes may be made without departing from the scope of the invention herein contemplated, it is intended that all matter contained in the foregoing description, including the accompanying drawings, shall be taken as being illustrative and not in a limiting sense.

What is claimed is:

1. In a wound dressing for covering a wound wherein an absorbent material for receiving and retaining wound fluids is sandwiched between opposed first and second perforated non-adherent sheet materials;

the improvement wherein the absorbent material is a multilayer structure comprising first and second absorbent layers, the first layer being a low density absorbent fabric having optimum absorption capacity for receiving wound fluids diffusing from the wound through the first perforated sheet material, the second layer being a high density absorbent fabric exhibiting optimum spreading or wicking characteristics for receiving and retaining wound fluid diffusing through the low density absorbent fabric, whereby to inhibit maceration caused by pooling of wound fluid on the wound surface.

2. A wound dressing as defined in claim 1 wherein the dressing is an island dressing.

3. A wound dressing as defined in claim 1 wherein the low density fabric has a density less than 0.1 gram per cubic centimeter and the high density fabric has a density on the order of 0.1 to 0.2 gram per cubic centimeter.

4. A wound dressing as defined in claim 1 wherein the absorbent material contains a third absorbent layer disposed on the outer surface of the second absorbent layer, the third absorbent layer being a low density absorbent fabric, whereby the absorbent material consists of a high density absorbent fabric sandwiched between outer layers of a low density absorbent fabric.

5. A wound dressing as defined in claim 1 wherein the first sheet material is of greater dimensions than the absorbent material, the absorbent material has a surface facing the second sheet material, and the first sheet material has edges defining its dimensions, which edges overlap and abut the surface of the absorbent material facing the second sheet material.

6. A wound dressing as defined in claim 5 wherein the second sheet material has a layer of pressure-sensitive adhesive on the surface facing the absorbent material; the absorbent material is of substantially smaller dimensions than the second sheet material; and the absorbent material is substantially centrally seated on the adhesive surface of the second sheet material, thereby providing an island dressing wherein the adhesive layer surrounding the absorbent material can secure the dressing to cover the wound.

\* \* \* \* \*